US012643993B2

(12) United States Patent
Dowling

(10) Patent No.: US 12,643,993 B2
(45) Date of Patent: *Jun. 2, 2026

(54) HYDROPHOBICALLY MODIFIED CHITOSAN COMPOSITIONS

(71) Applicant: Medcura, Inc., Riverdale, MD (US)

(72) Inventor: Matthew Dowling, Riverdale, MD (US)

(73) Assignee: Medcura, Inc., Riverdale, MD (US)

( * ) Notice: Subject to any disclaimer, the term of this patent is extended or adjusted under 35 U.S.C. 154(b) by 572 days.

This patent is subject to a terminal disclaimer.

(21) Appl. No.: 18/129,239

(22) Filed: Mar. 31, 2023

(65) Prior Publication Data

US 2023/0348699 A1 Nov. 2, 2023

Related U.S. Application Data

(63) Continuation of application No. 17/588,542, filed on Jan. 31, 2022, now Pat. No. 11,787,922, which is a continuation of application No. 16/592,234, filed on Oct. 3, 2019, now Pat. No. 11,274,194, which is a continuation-in-part of application No. PCT/US2018/027637, filed on Apr. 13, 2018.

(60) Provisional application No. 62/484,985, filed on Apr. 13, 2017.

(51) Int. Cl.
| | |
|---|---|
| *C08L 5/08* | (2006.01) |
| *A61L 15/26* | (2006.01) |
| *A61L 15/28* | (2006.01) |
| *A61L 24/08* | (2006.01) |
| *C08B 37/08* | (2006.01) |
| *C08L 71/00* | (2006.01) |

(52) U.S. Cl.
CPC ................ *C08L 5/08* (2013.01); *A61L 15/26* (2013.01); *A61L 15/28* (2013.01); *A61L 24/08* (2013.01); *C08B 37/003* (2013.01); *C08L 71/00* (2013.01)

(58) Field of Classification Search
CPC . C08L 5/08; C08B 37/003; C08B 3/16; C08B 3/18; C08B 11/193; A61K 31/717; A61K 31/722; A61K 31/734; A61K 31/737; A61K 9/00; A61K 9/703; A61L 15/26; A61L 15/28; A61L 15/42
USPC ......................................................... 536/20
See application file for complete search history.

(56) References Cited

U.S. PATENT DOCUMENTS

| | | | |
|---|---|---|---|
| 2,651,629 A | 9/1953 | White et al. | |
| 6,342,484 B1 | 1/2002 | Kulkarni et al. | |
| 6,517,678 B1 | 2/2003 | Shannon et al. | |
| 6,699,499 B1 | 3/2004 | Aneja et al. | |
| 8,664,199 B2 | 3/2014 | Dowling et al. | |
| 8,668,899 B2 * | 3/2014 | Dowling | A61L 24/0026 |
| | | | 424/94.6 |
| 8,858,883 B2 | 10/2014 | Dowling et al. | |
| 8,932,560 B2 | 1/2015 | Dowling et al. | |
| 9,066,885 B2 | 6/2015 | Raghavan et al. | |
| 9,616,088 B2 | 4/2017 | Diehn et al. | |
| 10,179,145 B2 | 1/2019 | Dowling et al. | |
| 10,493,094 B2 | 12/2019 | Diehn et al. | |
| 11,274,194 B2 * | 3/2022 | Dowling | A61K 31/717 |
| 11,787,922 B2 * | 10/2023 | Dowling | A61K 31/722 |
| | | | 536/20 |
| 2007/0156084 A1 | 7/2007 | Belhe et al. | |
| 2008/0064843 A1 | 3/2008 | Daly | |
| 2008/0254104 A1 | 10/2008 | Raghavan et al. | |
| 2010/0069536 A1 | 3/2010 | Sau | |
| 2011/0280857 A1 | 11/2011 | Dowling et al. | |
| 2012/0058970 A1 | 3/2012 | Dowling et al. | |
| 2012/0252703 A1 | 10/2012 | Dowling et al. | |
| 2014/0314706 A1 | 10/2014 | Diehn et al. | |
| 2015/0151005 A1 | 6/2015 | Bouchemal | |
| 2019/0159992 A1 | 5/2019 | Dowling | |
| 2020/0046870 A1 | 2/2020 | Dowling et al. | |
| 2020/0102446 A1 | 4/2020 | Dowling | |

FOREIGN PATENT DOCUMENTS

| | | | | |
|---|---|---|---|---|
| KR | 101106627 B1 * | 1/2012 | ............. | A61K 9/703 |
| WO | 2018184021 A1 | 10/2018 | | |
| WO | 2020181015 A1 | 9/2020 | | |

OTHER PUBLICATIONS

Lambers et al, International Journal of Cosmetic Science, 2006, Synopsis.*
Abdelaal et al., "Modification of chitosan derivatives of environmental and biological interest: A green chemistry approach", International Journal of Biological Macromolecules 55 (2013) 231-239.
Hu, et al., "Self-aggregation and antibacterial activity of N-acylated chitosan", ScienceDirect, Polymer 48 (2007) 3098-3106.

* cited by examiner

*Primary Examiner* — Ganapathy Krishnan
(74) *Attorney, Agent, or Firm* — Morgan, Lewis & Bockius LLP

(57) ABSTRACT

Disclosed herein is a polymer composition comprising an effective amount of a hydrophobically-modified polymer having functional groups along the backbone occupied by a fatty acid anhydride moiety. The polymer composition has a potent hemostatic action by gelling blood upon contact, and is suitable for treating internal and external bleeds. As disclosed herein, the modified polymer can be generated without the use of toxic reagents that would require removal from the product. Further, compositions are shelf stable even in a flowable form. That is, the hydrophobic grafts are not lost under product storage conditions (e.g., room temperature storage).

20 Claims, 4 Drawing Sheets

FIG. 2

  

| Blood Fraction | 5M C12/1M C18 1.5wt% | 5M C12/1M C18 1.0wt% | 5M C12 1.0wt% |
|---|---|---|---|
| Whole Blood | GELS | GELS | GELS* |
| Blood Cells in Saline | GELS | GELS | Almost Gels |
| Blood Cells in HBSS | GELS | GELS | Almost Gels |
| Plasma | GELS | Almost Gels | Almost Gels |
| Saline Only | GELS | NO | NO |
| DI Water | NO | NO | NO |
| LYSED Whole Blood | GELS | NO | GELS* |
| LYSED Blood Cells in Saline | GELS | Almost Gels | Almost Gels |
| LYSED Blood Cells in HBSS | GELS | Almost Gels | Almost Gels |

\* Does not gel immediately.

FIG. 3

| | C8 | C10 | C11 | C14 | C16 | C18 | Gels blood |
|---|---|---|---|---|---|---|---|
| | 1% | | | | | | No |
| | | 1% | | | | | No |
| | 5% | | | | | | No |
| | | 5% | | | | | Yes |
| | | | | | | 1.0% | Yes |
| | | | | | 1.0% | | Yes |
| | | | | 1.0% | | | Yes |
| | | | 5.0% | | | | Yes |
| | | 5.0% | | | | | Yes |
| | 10% | | | | | | No |
| | | | 2.5% | | | 1.0% | Yes |
| | | 2.5% | | | | 1.0% | Yes |
| | 10% | | | | | 1.0% | Yes |
| | | | 2.5% | | 1.0% | | Yes |
| | | 2.5% | | | 1.0% | | Yes |
| | 10% | | | | 1.0% | | Yes |
| | | | 2.5% | 1.0% | | | Yes |
| | | 2.5% | | 1.0% | | | Yes |
| | 10% | | | 1.0% | | | Yes |
| | | | 5.0% | | | 1.0% | Yes |
| | | 5.0% | | | | 1.0% | Yes |
| | 10% | | | | | 1.0% | Yes |
| | | | 5.0% | | 1.0% | | Yes |
| | | 5.0% | | | 1.0% | | Yes |
| | 10% | | | | 1.0% | | Yes |
| | | | 5.0% | 1.0% | | | Yes |
| | | 5.0% | | 1.0% | | | Yes |
| | 10% | | | 1.0% | | | Yes |

FIG. 4

| Sample | Type |
|--------|------|
| 1 | 1.0M C18 |
| 2 | 7.0M C12 |
| 3 | 2.5M C18 |
| 4 | 5.0M C12, 1.0M C18 |
| 5 | 5.0M C12, 2.5M C18 |

All samples were dissolved in 0.067 M lactic acid solution.

| Sample | Wt% | polymer:blood (v/v) ratio | |
|--------|-----|---------------------------|---------------------------|
| | | 1 to 1 | 1 to 0.5 |
| 1 | 0.5 | flowable | Flowable |
| 1 | 1.0 | Onset of gelation | Onset of gelation |
| 2 | 0.5 | Flowable | Gel |
| 2 | 1.0 | flowable (with chunks) | Gel |
| 3 | 0.5 | flowable | Flowable |
| 3 | 1.0 | Gel | Onset of gelation |
| 4 | 0.5 | Weak gel | Strong gel |
| 4 | 1.0 | Strong gel | Strong gel |
| 5 | 0.5 | Gel | Strong gel |
| 5 | 1.0 | gel | Gel |

HYDROPHOBICALLY MODIFIED CHITOSAN COMPOSITIONS

PRIORITY

This application is a continuation of U.S. application Ser. No. 17/588,542, filed Jan. 31, 2022, which is a continuation of U.S. application Ser. No. 16/592,234, filed Oct. 3, 2019 (now U.S. Pat. No. 11,274,194), which is a continuation-in-part of PCT/US2018/027637, filed Apr. 13, 2018, which claims the benefit of U.S. Provisional Application No. 62/484,985, filed Apr. 13, 2017, the contents of which are hereby incorporated by reference in their entireties.

BACKGROUND

Hydrophobically-modified chitosans have been described for use in hemostatic devices. See, U.S. Pat. No. 8,932,560, which is hereby incorporated by reference in its entirety. For example, to prepare hydrophobically-modified polymers, chitosans are reacted with alkyl aldehydes in aqueous acetic acid and ethanol, and the resulting Schiff bases are reduced to stable secondary amines by addition of a reducing agent such as sodium cyanoborohydride. However, a more cost effective and safe approach is desired for generating materials to be used for human and animal health care that will avoid the use of toxic reagents and generation of toxic byproducts that must be removed from the product.

The present invention addresses these and other objectives.

SUMMARY OF THE INVENTION

In various aspects and embodiments, the invention provides a polymer composition comprising an effective amount of a hydrophobically-modified polymer functional groups along the backbone occupied by a fatty anhydride moiety. The polymer composition has a potent hemostatic action by gelling blood upon contact, and is suitable for treating internal and external bleeds. As disclosed herein, the modified polymer can be generated without the use of toxic reagents that would require removal from the product. Further, compositions are shelf stable even in a flowable form. That is, the hydrophobic grafts are not lost under product storage conditions (e.g., room temperature storage).

In accordance with aspects of the current invention, the hydrophobically-modified polymer is prepared using fatty anhydride chemistry, resulting in amide bonds with the chitosan polymer and the hydrocarbon chains. While hydrolysis of amide bonds is generally known to occur in the presence of dilute acids, which acts as a catalyst for the reaction between the amide and water, the amide bonds formed between chitosan and alkyl anhydrides are shelf stable, even in the presence of dilute acids that are required to maintain solubility of the hydrophobically-modified chitosan. Accordingly, the modified polymers may be prepared using a one-pot synthesis, without the need for harsh reagents, including reducing agents. The materials can be precipitated following the reaction and dried for processing and incorporation into products, including solutions, gels, and foams, among others.

In various embodiments, the polymer has about 0.5% to about 10% of available amines having a substitution of a fatty anhydride moiety. In some embodiments, the polymer has less than about 10%, or less than about 3%, of available amines having a substitution of a fatty anhydride moiety. In some embodiments, the polymer has about 1% or about 2% of available amines substituted with a fatty anhydride moiety. In various embodiments, the fatty anhydride is a linear C14, C16, or C18 hydrocarbon moiety, which is optionally a saturated hydrocarbon.

In some embodiments, the hydrophobically-modified polymer has two or more (e.g., 2 or 3) different fatty anhydride groups conjugated along the polymer backbone. These polymers can provide a greater level of control over how these polymers interact with themselves and with other entities in an aqueous or organic environment. For example, the hydrophobically-modified polymer may have a population of C6 to C12 hydrocarbon groups, and a population of C14 to C18 hydrocarbon groups. In some embodiments, the hydrophobic groups further comprise C1 to C4 hydrocarbon groups. In still other embodiments, the hydrophobically-modified polymer consists or consists essentially of C14, C16, and/or C18 hydrocarbon moieties.

In some embodiments, the dilute acid is a weak organic acid. In some embodiments, the organic acid has a pKa of from about 2.5 to about 4.5, such as from about 3.0 to about 4.0. Exemplary organic acids include lactic acid, acetic acid, formic acid, citric acid, and malic acid. In some embodiments, the dilute organic acid is present in the composition at from 0.05M to 0.4M. In some embodiments, the polymer is formulated with about 0.05M to about 0.2M of the organic acid, such as lactic acid. In some embodiments, the polymer is formulated with about 0.1M lactic acid. In some embodiments, the composition will have a pH of less than about 5, or less than about 4, or less than about 3. While these organic acids are suitable for solubilizing the hydrophobically-modified chitosan, they do not substantially catalyze hydrolysis of the amide bond between the chitosan and the hydrophobic graft.

A hydrophobically-modified biopolymer material for incorporation into aqueous or organic solutions or suspensions can be based on a solution of the hm-biopolymer that is about 0.1% to about 5.0% by weight relative to the total weight of the composition. In some embodiments, the hm-chitosan is present at about 0.5% to about 4%, or about 0.5% to about 3% of the total weight of the composition, or about 0.5% to about 2% of the total weight of the composition.

In various embodiments, the composition can be applied to various wound dressings, and dried or lyophilized for use. In some embodiments, the composition is used to coat bandages for wound care.

In exemplary embodiments, the invention provides a polymer composition comprising a hydrophobically-modified chitosan in a dilute organic acid, the hydrophobically-modified chitosan comprising from about 0.1% to about 5% of available amines substituted with C14 to C18 fatty anhydride groups. In some embodiments, the hydrophobically-modified chitosan comprises from about 0.5% to about 3% of available amines substituted with C14 to C18 fatty anhydride groups. In some embodiments, the hydrophobically-modified chitosan comprises from about 1% to about 2% of available amines substituted with C14 to C18 fatty anhydride groups. The chitosan is generally a medium molecular weight chitosan, for example, has an average molecular weight of from about 40,000 to about 500,000 Daltons (e.g., about 250 kDa). The amount of deacetylation for purposes of determining grafting density is considered to be about 85%. In these embodiments, the hydrophobically-modified polymer is present at about 0.1 to about 5% by weight of the composition, or in some embodiments is present at from about 1 wt % to about 3 wt %, or is present at from about 1.5 wt % to about 2.5 wt %. The dilute organic acid may be an organic acid having a pKa of from about 2.0 to about 4.5 as described. Exemplary organic acids include lactic acid, acetic acid, or citric acid, among others. In some embodiments, the dilute organic acid has a pKa of from about 3.0 to about 4.0, which may be present in the composition from 0.05M to 0.4M, or about 0.1M to 0.2M. In some embodiments, the dilute organic acid is lactic acid.

In other aspects, the invention provides a method for treating a wound. The method comprises applying the polymer composition described herein to a wound or bleed. The wound or bleed can be an external wound or bleed, or an internal wound or bleed. In some embodiments, the wound has high exudate or blood flow. In some embodiments, the invention provides a topical solution or gel for local management of bleeding such as laceration and minor bleeding. The composition can be easily applied by the patient or by an untrained user, and will quickly stop even strong bleeds by forming an artificial clot or seal. The composition can be used with wound dressings and bandages, either separately or as a combined product.

Other aspects and embodiments of the invention will be apparent from the following detailed description.

DESCRIPTION OF THE FIGURES

FIG. 2 shows the results of blood gelation experiments using hydrophobically-modified chitosans prepared using anhydride chemistry. A 1.0 mL sample of each hm-chitosan solution was mixed with 0.5 mL of each blood fraction and vortexed thoroughly. Modified polymer compositions include: (1) 5% C12, 1% C18, 1.5 wt %; (2) 5% C12, 1% C18, 1.0 wt %; and (3) 5% C12, 1.0 wt %.

FIG. 3 shows the results of blood gelling capability of various hydrophobic grafting designs along chitosan backbone. Each construct was prepared using anhydride chemistry. All hydrophobic design grafts are attached to a medium molecular weight chitosan (Primex hqg 400). Solutions of hm-chitosans were 1.5 wt % of polymer dissolved in 0.2 M acetic acid in water. Several 2nd, 3rd and 4th order grafting designs are described via % of amines along the chitosan backbone. Gelling is defined as an ability for a mixture of polymer and blood (citrated bovine blood (Lampire)) as a ratio of 2:1 (v/v) to hold its own weight upon vial inversion.

FIG. 4 shows blood gelation experiments with 5 different hm-chitosan constructs at different wt % (0.5 and 1.0 wt %) and at different ratios with blood. Samples 4 and 5, incorporating C12 and C18 hydrophobic grafts, showed the strongest gelation properties.

DETAILED DESCRIPTION OF THE INVENTION

Figure 1:
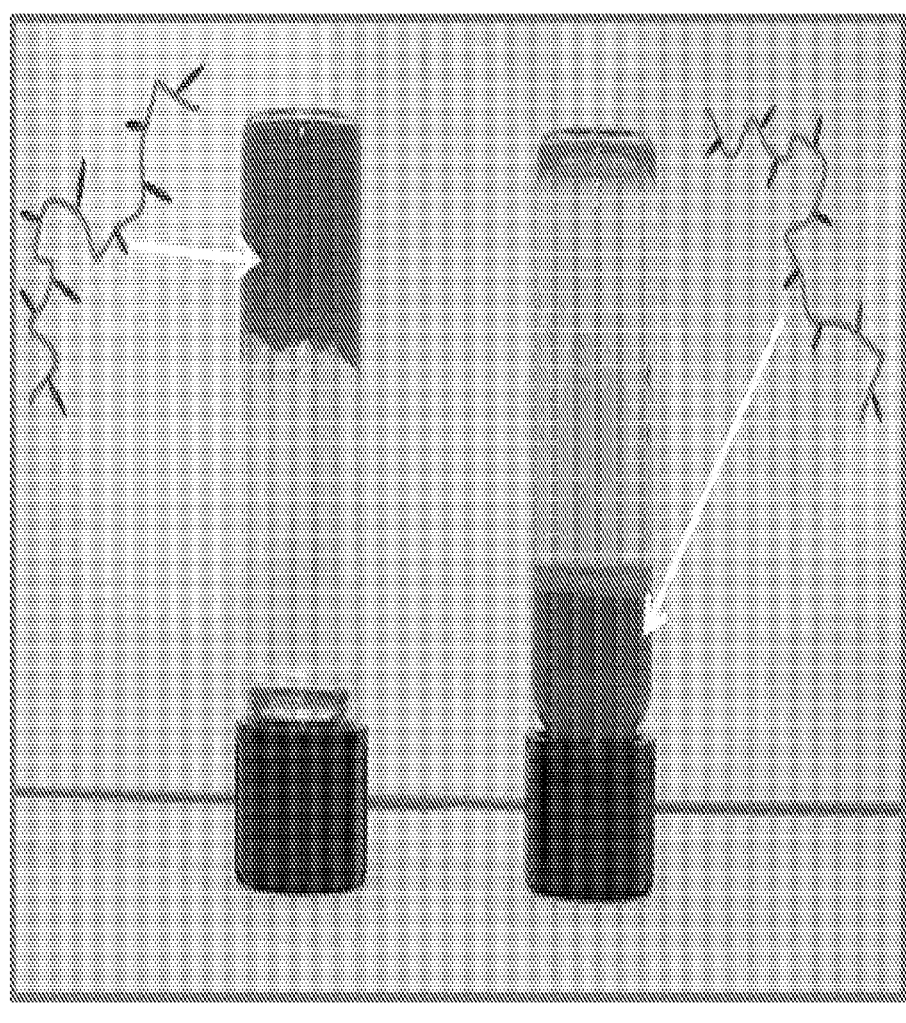
FIG. 1 shows a blood gelling experiment. The left panel illustrates a successful construct, where hydrophobically-modified chitosan mixed with blood forms a gel that can hold its own weight upon inversion of the vial. The right panel illustrates an unsuccessful construct.

In various aspects and embodiments, the invention provides a polymer composition comprising an effective amount of a hydrophobically-modified polymer having functional groups along the backbone occupied by a fatty anhydride moiety. The polymer composition has a potent hemostatic action by gelling blood upon contact, and is suitable for treating internal and external bleeds. As disclosed herein, the modified polymer can be generated without the use of toxic reagents that would require removal from the product. Further, compositions are shelf stable even in a flowable form. That is, the hydrophobic grafts are not lost under product storage conditions (e.g., room temperature storage).

In various embodiments, the polymer is a hydrophobically-modified polymer having available amine groups, such as chitosan. Chitosan is the common name of the linear, random copolymer that consists of $\beta$-(1-4)-linked D-glucosamine and N-acetyl-D-glucosamine. The molecular structure of chitosan consists of a linear backbone linked with glycosidic bonds. Chitosan is the major component of crustacean shells such as crab, shrimp, krill and crawfish shells. Additionally, chitosan is the second most abundant natural biopolymer after cellulose. Commercial chitosan samples are typically prepared by chemical de-N-acetylation of chitin under alkaline conditions. Depending on the source of the natural chitin (extracted from shells) and its production process, chitosan can differ in size (average molecular weight, Mw) and degree of N-acetylation (% DA). While the poor solubility of chitosan in water and in common organic solvents restricts its applications, reactive amino groups in the chitosan backbone make it possible to chemically conjugate chitosan with various molecules and to modulate its properties.

The degree of deacetylation of chitin may range from about 40-100%, or in some embodiments, from 60 to 100%, which determines the charge density. The structure of chitosan (deacetylated) is depicted in Formula 1 below:

These repeating monomeric units include a free amino group, which makes molecules or compounds containing chitosan or its derivatives readily reactive. The hydrophobic modification of the chitosan backbone is commonly through the association of an amphiphilic compound (e.g., fatty aldehyde) with the amino group, such that the hydrophobic tail of the amphiphilic compound is bound with the hydrophilic backbone structure. For example, to prepare hydrophobically-modified polymers, chitosans have been reacted with alkyl aldehydes in aqueous acetic acid and ethanol, and the resulting Schiff bases are reduced to stable secondary amines by addition of a reducing agent, such as sodium cyanoborohydride. See, U.S. Pat. No. 8,932,560, which is hereby incorporated by reference in its entirety. These secondary amine groups are very stable, but the process is time-consuming, and cyanoborohydride is a toxic reagent that cannot be present in the final product.

In accordance with aspects of the current invention, the hydrophobically-modified polymer is prepared using fatty anhydride chemistry, resulting in amide bonds with the chitosan polymer and the hydrocarbon chains. Amide bonds can generally be susceptible to hydrolysis in solution. Hydrolysis of amide bonds is generally known to occur in the presence of acids, which act as catalysts for the reaction between the amide and water. Amides are also susceptible to alkaline hydrolysis. However, as demonstrated herein, the amide bonds formed between chitosan and alkyl anhydrides are shelf stable, even in the presence of dilute acids that are required to maintain solubility of the hydrophobically-modified chitosan. Accordingly, the modified polymers may be prepared using a one-pot synthesis, without the need for harsh reagents, including reducing agents. The materials can be precipitated following the reaction and dried for processing and incorporation into products, including solution, gels, and foams, among others.

In some embodiments, the hm-chitosan is derived from a deacteylated chitin, which may be derived from one or more of crab, shrimp, krill, and crawfish.

In various embodiments, the biopolymer is a hm-chitosan, which may be prepared from a chitosan having a degree of deacetylation of from about 40% to about 90%, such as from about 50% to about 90%, such as from about 60% to about 90%. In some embodiments, the degree of deacteylation is about 85%. In some embodiments, the degree of substitution of the hydrophobic substituent on the chitosan is from about 1% to about 50% of the available amine groups. In some embodiments, the degree of substitution of the hydrophobic substituent on the chitosan is from about 1% to about 20% of the available amine groups, or from about 1% to about 10% of the available amine groups, or from about 1% to about 5% of the available amine groups. Generally, larger hydrocarbon substituents will require less grafting density. In some embodiments, the molecular weight of the chitosan is from about 25,000 to about 1,500,000 grams per mole. In various embodiments, the molecular weight of the biopolymer ranges from about 40,000 to about 500,000 grams per more, or from about 50,000 to about 250,000 grams per mole, or from about 50,000 to about 100,000 grams per mole. As used herein, the term "molecular weight" means weight average molecular weight. Methods for determining average molecular weight of bio-polymers include low angle laser light scattering (LLS) and Size Exclusion Chromatography (SEC). In performing low angle LLS, a dilute solution of the polysaccharide, typically 2% or less, is placed in the path of a monochromatic laser. Light scattered from the sample hits the detector, which is positioned at a low angle relative to the laser source. Fluctuation in scattered light over time is correlated with the average molecular weight of the polysaccharide in solution. In performing SEC measurements, again a dilute solution of biopolymer, typically 2% or less, is injected into a packed column. The polysaccharide is separated based on the size of the dissolved polymer molecules and compared with a series of standards to derive the molecular weight.

In some embodiments, the polymeric component is a mixture of polysaccharides. For instance, the mixture may include two or more different classes of natural polymers, for instance the chitosan and a cellulosic, or the chitosan and an alginate, or a mixture of the chitosan, an alginate, and a cellulosic.

In various embodiments, the polymer has about 0.5% to about 10% substitution of available amines by a fatty anhydride moiety. In some embodiments, the polymer has less than about 10% of available amines substituted by a fatty anhydride moiety, or less than about 3% of available amines substituted by a fatty anhydride moiety. In some embodiments, the polymer has about 1% or about 2% of available amines substituted with a fatty anhydride moiety. In various embodiments, the fatty anhydride is a linear C14, C16, or C18 hydrocarbon moiety, which is optionally a saturated hydrocarbon.

In some embodiments, the hydrophobically-modified polymer has two or more (e.g., 2 or 3) different fatty anhydride groups conjugated along the polymer backbone. These polymers can provide a greater level of control over how these polymers interact with themselves and with other entities in an aqueous or organic environment. For example, the hydrophobically-modified polymer may have a population of C6 to C12 hydrocarbon groups, and a population of C14 to C18 hydrocarbon groups. In some embodiments, the hydrophobic groups further comprise C1 to C4 hydrocarbon groups. In exemplary embodiments, the hydrophobic groups comprise a population of C1 to C4 hydrocarbon moieties, a population of C6 to C12 hydrocarbon moieties, and a population of C14 to C18 hydrocarbon moieties. In still other embodiments, the hydrophobically-modified polymer consists or consists essentially of C14, C16, and/or C18 hydrocarbon moieties. In these embodiments, the hydrophobically-modified chitosan may have from about 5% to about 20% or from about 5% to about 10% of available amines substituted with a hydrocarbon group.

In some embodiments, the composition is a hemostatic device or dressing for bleeding control. There are a myriad of material characteristics that are desired for a well-functioning hemostatic material, including: (1) the material should be easy to apply (ideally flowable to conform to surfaces, cavities, and/or small areas), (2) able to create a rapid seal when in contact with bleeding tissue, (3) retain its mechanical integrity in the face of high pressure bloodflow, (4) be easy to remove, and (5) be safely bioresorbable if left inside the body after use. While a single material that provides tunability in each of these categories would be ideal, such a material is difficult to design, because often chemistries which result in a favorable attribute in one area (e.g. adhesion), result in the detuning of attributes in another area (e.g. cohesion). Here, we describe a framework, utilizing the available chemistry along the chitosan backbone, free amine groups, to create specific hydrophobic designs that employ multiple different grafting lengths and density of hydrophobic groups to achieve optimized properties in flowability, tissue adhesion, cohesion, biodegradation, and removability. Further, the use of amide bonds to couple the hydrophobic groups allows for degradation of the polymer through action of amidases, which are replete in biological systems.

In some embodiments, the modified polymer has both C8 and C18 acyl groups covalently attached to the backbone of the biopolymer, which is both adhesive to tissues, due to the C8 groups, and also cohesive under exudate flow, due the C18 groups. The C8 groups are fluid at room and body temperature, allowing the polymer to spread onto the cell surfaces more effectively, whereas the C18's on neighboring polymer chains hold the polymer molecules together strongly even in the presence of high exudate or blood flow. These embodiments can thus balance adhesive and cohesive properties. Traditional chitosan dressings fail due to either lack of adherence to the wound site or lack of coherence once an initial seal has been achieved. More specifically, native chitosan is particularly good at adhering to wet, bleeding tissue. However, chitosan generally has a limited ability to hold together under high-pressure blood flow.

In accordance with embodiments of the invention, certain hydrophobes provide advantages for optimizing adherence (e.g., to the tissue or wound site), and other hydrophobes are more advantageous for improving coherence (e.g., coherence of the artificial clot). As used herein, the term "artificial clot" refers to physical networks of hydrophobically-modified polymers, blood cells, and surrounding tissue cells which effectively act as a solid barrier to prevent further blood loss. In the range of C6-C12 lengths, the hydrophobic grafts are useful in improving adhesion of the dressings. In the range of C13-C22 lengths, the hydrophobic grafts are useful in improving the cohesion of the dressings. By mixing hydrophobic grafts, for example, C12 and C18 attached to a composition has altered characteristics as compared to native chitosan, 5% C12 chitosan only, or 1% C18 chitosan only. In some embodiments, the polymer has from about 1% to about 10% of available amines occupied by a C12 hydrophobic group, or about 5% of available amines are occupied by a C12 hydrophobic group. In some embodiments, the polymer has from about 0.5% to about 5% of available amines occupied by C18 hydrophobic groups, such as from about 0.5% to about 2% (e.g., about 1%) of available amines occupied by C18 hydrophobic groups. These may be present for example on medium molecular weight chitosan (i.e., average MW of about 200 to about 300 kDa), and having a degree of deacetylation of from 70% to about 100%.

For example, in some embodiments, the hemostat composition is a topical solution or gel, and may be syringable gel. The C12 component allows for robust attachment of the gel to the mucosal surface, whereas the C18 component allows for cohesive matrix properties as the blood begins to infiltrate the gel. In some embodiments, the gel comprises only C14, C16, and/or C18 hydrophobic grafts, which provides the necessary activity and cohesion for topical products, even for wounds with high blood flow or exudate.

In some embodiments, the hemostat composition is a lyophilized sponge. The dressing not only adheres strongly to the bleeding tissue (relative to native chitosan), but also holds together in the presence of significant blood pressure. While a single-length 5 mol % C12 adheres significantly more than native chitosan to wet tissue, it fails upon application of blood pressures much greater than 100 mmHg. Particularly during resuscitation after trauma, there can be a significant risk of re-bleeding at resuscitation pressures.

In some embodiments, the hemostat composition is a clear film. The film not only adheres strongly to the bleeding tissue (relative to native chitosan), but also holds together in the presence of significant blood pressure. While a single-length 5 mol % C12 adheres significantly more than native chitosan to wet tissue, it fails upon application of blood pressures much greater than 30 mmHg. An ability to stand up to such pressures creates an issue in most clinical bleeding scenarios.

In some embodiments, the hemostat composition is a powder. The powder not only adheres strongly to bleeding tissue (relative to native chitosan), but also holds together in the presence of significant blood pressure. While a single-length 5 mol % C12 powder adheres significantly more than native chitosan to wet tissue, it fails upon application of blood pressures much greater than 100 mmHg. Again, during resuscitation after trauma, there can be a significant risk of re-bleeding at resuscitation pressures.

In some embodiments, the hemostat composition is a foam, including a sprayable or syringable foam. The C12 component of the formulation allows for large expansion of the foam relative to the initial gel volume, whereas the C18 component allows for a mechanically integral final foam product. Further, foams can employ a double barrel format, as described in WO 2018/184021, which is hereby incorporated by reference in its entirety.

In some embodiments, the hemostat composition is a moldable putty. Hydrophobically-modified chitosan in the form of a moldable putty composition is described in U.S. Pat. No. 9,616,088, which is hereby incorporated by reference in its entirety. For example, the gel at 1.0 wt % (in aqueous 0.15 M lactic acid) is thick, but has an ability to mix with polyvinyl alcohol and sodium tetraborate to create a putty-like mechanical characteristic. The C12 component of the formulation allows for robust attachment of the putty to the mucosal surface, whereas the C18 component allows for cohesive matrix properties as the blood begins to infiltrate the putty.

Alternatively, or in addition, incorporation of small hydrophobic groups, such as C1 to C4 acyl chains, allows the chitosan to degrade more predictably from lysozyme activity in the body. This is very important for creating a material which can be left inside the body after treatment of the wound. More specifically, hydrophobic groups below the length of C6 do not contribute towards improved hemostatic effect. However, hydrophobic modification in the range of C1 to C6 allow for a framework to optimize the degradation of the material inside the body via lysozymes. Particularly in the case of surgical-use hemostats, it is ideal for the hemostatic biomaterial to degrade quickly after achieving hemostasis. For example, 5% C12 and 30% C1 (with respect to available amines) attached to a medium molecular weight chitosan (MW~250 kDa) creates a composition having improved biodegradation characteristics relative to either native chitosan, 5% C12 chitosan only, or 30% C1 chitosan only. Other variations, including with C6 to C12 (e.g., C8 or C10 or C12) and C14 to C18 hydrocarbon groups are described herein. In some embodiments, C1 to C4 acyl chains are incorporated at from 10% to 80%, such as from 10% to 60%. In some embodiments, the C1 to C4 acyl chains are incorporated at about 20% to about 60%, or from about 20% to 50%, or from 20% to 40%.

In various embodiments, the composition is formulated as a liquid, gel, or foam. That is, the composition may be a flowable product, and may be suitable for topical application to wounds or bleeds, both for internal and external use. In some embodiments, the composition comprises at least one synthetic polymer. Exemplary synthetic polymers include polythenes, polystyrenes, polyacrylates, polyamides, polyesters, polyurethanes, polysulfides, and polycarbonates. In some embodiments, the synthetic polymer is polyethylene glycol. In some embodiments, the synthetic polymer is polyvinyl alcohol. Inclusion of synthetic polymers can modify the physical properties of the composition, including the viscosity as well as the cohesion of the composition or of the artificial clot or seal created upon use. In some embodiments, the composition can be crosslinked to create various additional functionalities, including moldable putties. See U.S. Pat. No. 9,616,088, which is hereby incorporated by reference in its entirety.

In some embodiments, the dilute acid is a weak organic acid. An organic acid is an organic compound with acidic properties. The most common organic acids are the carboxylic acids, whose acidity is associated with their carboxyl group-COOH. For example, the organic acid may have a pKa of from about 2 to about 5, or from about 2.5 to about 4, or from about 3 to about 4, or from about 3.5 to about 4. Exemplary organic acids include lactic acid, acetic acid, formic acid, citric acid, and malic acid. In some embodiments, the organic acid is lactic acid, acetic acid, or citric acid. In some embodiments, the dilute acid is from 0.05M to 0.4M of the organic acid, such as lactic acid. In some embodiments, the polymer is formulated with about 0.05M to about 0.2M lactic acid. In some embodiments, the polymer is formulated with about 0.1M lactic acid. In some embodiments, the composition will have a pH of less than about 5, or less than about 4, or less than about 3. In some embodiments, the pH of the composition is from about 2 to about 4. While these organic acids are suitable for solubilizing the hydrophobically-modified chitosan, they do not substantially catalyze hydrolysis of the amide bond between the chitosan and the hydrophobic graft.

A hydrophobically-modified biopolymer material for incorporation into aqueous or organic solutions or suspensions can be based on a solution of the hm-biopolymer that is about 0.1% to about 5.0% by weight relative to the total weight of the composition. In some embodiments, the hm-chitosan is present at about 0.5% to about 4%, or about 0.5% to about 3% of the total weight of the composition, or about 0.5% to about 2% of the total weight of the composition. In some embodiments, the biopolymer is about 1.0% to about 5.0% by weight relative to the total weight of the composition, or in some embodiments, about 1.5% to about 5%, or about 2.0% to about 4% of the total weight of the composition. In some embodiments, the hydrophobically-modified polymer is present at from about 1 wt % to about 3 wt %, or from about 1.5 wt % to about 2.5 wt %.

In various embodiments, the composition can be applied as a solution, gel, or foam, to various wound dressings, and dried or lyophilized for use. In some embodiments, the composition is used to coat bandages for wound care.

In some embodiments, the modified polymer may provide anti-bacterial and/or anti-fungal properties, which provide unique advantages. See, for example, PCT/US2017/56887 and WO 2017/177027, which are hereby incorporated by reference in their entireties.

While the mechanism of action of chitosan as an anti-microbial is a not well understood, two key contributing mechanisms likely play a role: (1) penetration into the bacterial cells and intercalation with DNA, thus preventing replication, and (2) physical immobilization of cells due to physical binding of bacteria into a robust cohesive network. Smaller hydrophobes (e.g., C1-C12) assist with interfacing with the cell membrane and/or cell wall, and larger hydrophobes (e.g., C13-C22) may assist with physical binding of the bacteria into immobilized networks. Hence, the variable-length design framework, along a wide span of polymer (e.g., chitosan) backbone lengths, allows for the creation of many unique molecules which can amplify a given mechanism towards bacterial death depending upon the clinical circumstances. Certain bacteria are more susceptible to penetration through the cell well (typically gram negative); infections caused robust bacteria may be limited to treatment via molecules that work only by physical bacteriostasis.

In exemplary embodiments, the invention provides a polymer composition comprising a hydrophobically-modified chitosan in a dilute organic acid, the hydrophobically-modified chitosan comprising from about 0.1% to about 5% of available amines occupied by C14 to C18 fatty anhydride groups. In some embodiments, the hydrophobically-modified chitosan comprises from about 0.5% to about 3% of available amines occupied by C14 to C18 fatty anhydride groups. In some embodiments, the hydrophobically-modified chitosan comprises from about 1% to about 2% of available amines are occupied by C14 to C18 fatty anhydride groups. The chitosan is generally a medium molecular weight chitosan, for example, having an average molecular weight of from about 40,000 to about 500,000 Daltons (e.g., about 250 kDa), and has a degree of deacetylation of from about 50% to about 100% (e.g., about 85%). In these embodiments, the hydrophobically-modified polymer is present at about 0.1 to about 5% by weight of the composition, or in some embodiments is present at from about 1 wt % to about 3 wt %, or is present at from about 1.5 wt % to about 2.5 wt %. The dilute organic acid may be an organic acid having as pKa as described (e.g., pKa of 2 to 5, or 2 to 4, or 3 to 4). Exemplary organic acids include lactic acid, acetic acid, or citric acid, among others. In some embodiments, the dilute organic acid is present at from about 0.05M to about 0.4M in the composition, or is present at about 0.1M to about 0.2M in the composition. In some embodiments, the dilute organic acid is lactic acid.

In other aspects, the invention provides a method for treating a wound. The method comprises applying the polymer composition described herein to a wound or bleed, including acute and chronic wounds. The wound or bleed can be an external wound or bleed, or an internal wound or bleed. In some embodiments, the wound has high exudate or blood flow. In some embodiments, the invention provides a topical solution or gel for local management of bleeding such as laceration and minor bleeding. The composition can be easily applied by the patient or by an untrained user, and will quickly stop even strong bleeds by forming an artificial clot or seal. The composition can be used with wound dressings and bandages, either separately or as a combined product.

In various embodiments, the wound is a heavily exuding chronic wound or acute wound, and may be a pressure sore, diabetic ulcer, leg ulcer, donor site and/or graft site, surgical wound, skin abrasion or laceration, 1st and 2nd degree burn, or trauma wound. In other embodiments, the wound is a minor cut, minor scald, 1st degree burn, abrasion, or laceration. In some embodiments, the composition is a syringable product that is applied during surgery to control bleeding.

In some embodiments, the polymer composition provides advantages in tissue adhesion as well as material cohesion (for creating a barrier even with high blood flow). In some embodiments, the material degrades in the body within one month, or within two weeks, or within one week, or with about two days. In some embodiments, the material is mechanically removable from the wound without damaging the underlying tissue. In various embodiments, the modified polymer (in the amount employed) is soluble in aqueous environment.

As used herein, the term "about" means ±10% of the associated numerical value.

EXAMPLES

Example 1: Hydrophobic Modification of Chitosan at Lab Scale; Synthesizing Hm-Chitosan Using Dodecandoic Anhydride and Palmitic Anhydride Two grams of chitosan was dissolved in 100 mL of 0.2 M acetic acid by stirring for 30 minutes in a beaker covered with aluminum foil. The solution was filtered using a vacuum filter. Once the chitosan solution was poured from the flask into a 600 ml beaker, 100 mL of ethanol was added to the flask gradually and swirled around to remove the remaining chitosan on the sides of the flask. The ethanol and remaining chitosan was poured into the beaker with the rest of the chitosan and the solution was heated to 60° C.; the pH was adjusted to 6.0 by dropwise addition of 0.5 M NaOH. In a separate beaker, 20 mL of ethanol was added to a mixture of dodecanoic anhydride (0.24 g for 5% modification) and palmitic anhydride (0.061 g for the 1% modification); the solution was also heated to 60° C. to fully dissolve the fatty anhydrides, and it was then slowly poured into the chitosan solution. The mixture was stirred for 24 hours under heat and the hm-chitosan was then precipitated from the solution by adding 0.2 M sodium hydroxide dropwise.

Example 2: Hydrophobic Modification of Chitosan; Synthesizing Hm-Chitosan as Acid-Salt Film Using Palmitic Anhydride This procedure describes a batch manufacturing process of hydrophobically-modified chitosan acid-salt. About 200 g of chitosan is solubilized in a reaction vessel in about 10 L volume, with about 114 mL of glacial acetic acid in water. The volume is then brought to 20 L with addition of ethanol. The solution is heated and maintained at about 65° C. About 9.7 g of palmitic anhydride solubilized in about 2000 mL of ethanol is slowly transferred to the reaction vessel, and the temperature maintained around 65° C. with constant stirring. The reaction is allowed to continue for at least 1 hour with continued stirring. To precipitate the hydrophobically-modified chitosan, sodium hydroxide is added slowly while stirring. Precipitation is allowed to occur for at least one hour.

The precipitate is washed with ethanol and then rinsed with water for several minutes. Excess water is then removed. Washed hydrophobically-modified chitosan is added to 10 L of water in a reaction vessel with stirring, and about 285 mL glacial acetic acid is added. Hydrophobically-modified chitosan is allowed to dissolve and reach a temperature of about 62° C. The hydrophobically-modified chitosan solution is poured into aluminum sheet pans and dried for at least 24 hours in a forced air oven set to about 60° C.

The resulting hydrophobically-modified films can be shred into small pieces. Material may be ground and solubilized in dilute acid to form a hydrogel, or incorporated with other materials, including bandages.

Example 3: Blood Gelation Experiments with Hydrophobically-Modified Chitosan Employing Anhydride Chemistry For many applications, a flowable product that gels specifically in the presence of intact blood cells would be desirable. FIG. 2 shows example blood gelation experiments. A 1.0 mL sample of each anhydride hm-chitosan solution was mixed with 0.5 mL of each blood fraction and vortexed thoroughly. Modified polymer compositions include (1) 5% C12, 1% C18, 1.5 wt %; (2) 5% C12, 1% C18, 1.0 wt %; and (3) 5% C12, 1.0 wt %. As shown, construct (1) formed a gel even in saline alone as well as with lysed blood cells and plasma. Less hydrophobic properties than construct (1) would be desirable for flowable products. Constructs (2) and (3) show that decreasing the hydrophobic character improved properties of the material for use in flowable products.

FIG. 3 shows the results of blood gelling capability of various hydrophobic grafting designs along chitosan backbone. All hydrophobic design grafts are attached to a medium molecular weight chitosan (Primex hqg 400). Solutions of hm-chitosans were 1.5 wt % of polymer dissolved in 0.2 M acetic acid in water. Several 2nd, 3rd and 4th order grafting designs are described via % of amines along the chitosan backbone. Gelling is defined as an ability for a mixture of polymer and blood (citrated bovine blood (Lampire)) as a ratio of 2:1 (v/v) to hold its own weight upon vial inversion. As shown, 1.0% C14, C16, or C18 were sufficient for gelling blood and demonstrated good physical properties for flowable products. C8, C10, and C12 grafts can also be added to alter the properties.

FIG. 4 shows blood gelation experiments with 5 different hm-chitosan constructs at different wt % (0.5 and 1.0 wt %) and at different ratios with blood. Samples 4 and 5, incorporating C12 and C18 hydrophobic grafts, showed the strongest gelation properties. Generally, compositions comprising 1.0 wt % of polymer performed well.

Example 4: Stability of Hydrophobically-Modified Chitosan Employing Anhydride Chemistry A sterile topical gel was made by hydrophobically-modifying chitosan with palmitic anhydride essentially as described in Example 2. The hydrophobically-modified chitosan was combined with 1% w/w lactic acid to solubilize polymer (2 wt % polymer dissolved in 0.1M lactic acid in water). The hydrophobically-modified polymer was also evaluated in a bandage form, in which the hydrophobically-modified chitosan coats a cellulose pad on a soft bandage backing. Gels and bandages were aged to 12 and 14 months, and tested alongside non-aged gels and bandages.

In vivo studies were conducted in a controlled acute swine model of external hemorrhage via skin laceration to evaluate the materials. Specifically, adult, Yorkshire swine were anesthetized and dorsal sides exposed. Using a scalpel blade, an incision measuring 5 mm deep×8 mm long was made into the skin and the site was allowed to bleed for 20 seconds. The incision was then wiped with a gauze pad and the test material, either the Bandage or Gel was applied with digital pressure for 20 seconds. Pressure was then withdrawn for 2 minutes, during which time the site was observed for continued bleeding. If further bleeding did not occur, another skin incision was made on that pig, for a total of 30 incisions per animal. If bleeding continued during the 2 minute observation period, another round of 20 seconds of pressure followed by 2 minutes observation was made. A total of 30 incisions were made. For each incision, the number of compression/observation cycles required to achieve hemostasis was recorded.

Student's t-statistic was used to compare the number of compression/observation cycles needed to achieve hemostasis in the treatment groups. Statistical significance is defined as a p-value less than 0.05. A summary table indicating the number of cycles required to achieve hemostasis with each path is indicated in Table 1. All materials performed well.

TABLE 1

| Results of Bleeding Studies | | | | | |
|---|---|---|---|---|---|
| | Number of Compression Cycles Required to Achieve Hemostasis | | | | |
| Test Material | 1 | 2 | 3 | 4 | 5 |
| Bandage aged to 12 months, measuring 19 mm × 76 mm. Bandage is composed of soft, white, sterile non-woven palmitic-N-acetylglucosamine | 15 | 0 | 0 | 0 | 0 |

TABLE 1-continued

Results of Bleeding Studies

| Test Material | Number of Compression Cycles Required to Achieve Hemostasis | | | | |
| --- | --- | --- | --- | --- | --- |
| | 1 | 2 | 3 | 4 | 5 |
| (chitosan) with a flexible woven fabric adhesive backing. (N = 15) | | | | | |
| Bandage aged to 12 months, measuring 19 mm × 76 mm. Bandage is composed of soft, white, sterile non-woven palmitic-N-acetylglucosamine (chitosan) with a flexible woven fabric adhesive backing. (N = 15) | 15 | 0 | 0 | 0 | 0 |
| Gel aged to 12 months. Viscous semi-transparent gel composed of palmitic-N-acetylglucosamine (chitosan) dissolved in dilute lactic acid (0.1M). (N = 15) | 15 | 0 | 0 | 0 | 0 |
| Gel aged to 14 months. Viscous semi-transparent gel composed of palmitic-N-acetylglucosamine (chitosan) dissolved in dilute lactic acid (0.1M). (N = 15) | 15 | 0 | 0 | 0 | 0 |

What is claimed is:

1. A polymer composition comprising an effective amount of a hydrophobically-modified chitosan, the hydrophobically-modified chitosan having hydrocarbon groups attached to the chitosan backbone through amide linkages, wherein the composition is formulated with a pH of about 5 or less and is in the form of a gel, film, powder, foam or putty,
    wherein the hydrophobic groups comprise C1 to C4 hydrocarbon groups and a hydrocarbon greater than C6, and
    wherein the C1 to C4 hydrocarbon groups are present at 20 mol % to 40 mol % with respect to amine groups of chitosan.

2. The polymer composition of claim 1, wherein the polymer composition is a gel.

3. The polymer composition of claim 1, wherein the polymer composition is a film.

4. The polymer composition of claim 1, wherein the polymer composition is a powder.

5. The polymer composition of claim 1, wherein the polymer composition is a foam.

6. The polymer composition of claim 1, wherein the polymer composition is a putty.

7. The polymer composition of claim 1, wherein the hydrophobically-modified chitosan has about 1% to about 10% of available amines substituted with the greater than C6 hydrocarbon group.

8. The polymer composition of claim 7, wherein the hydrophobically-modified chitosan has less than about 3% of available amines substituted with the greater than C6 hydrocarbon group.

9. The polymer composition of claim 8, wherein at least one hydrocarbon group is a linear C14, C16, or C18 hydrocarbon moiety.

10. The polymer composition of claim 9, wherein the chitosan is a medium molecular weight chitosan.

11. The polymer composition of claim 1, wherein the hydrophobically-modified chitosan has 2 or 3 different hydrocarbon groups conjugated along the chitosan backbone.

12. The polymer composition of claim 11, having a population of C6 to C12 hydrocarbon groups, and a population of C14 to C18 hydrocarbon groups.

13. The polymer composition of claim 1, wherein the composition is formulated in a dilute organic acid, the organic acid having a pKa of from about 2 to about 5.

14. The polymer composition of claim 13, wherein the organic acid is lactic acid, acetic acid, formic acid, or malic acid.

15. The polymer composition of claim 13, wherein the hydrophobically-modified chitosan is present at 0.1 to about 5% by weight.

16. The polymer composition of claim 13, wherein the organic acid is present in the composition from about 0.05M to 0.4M.

17. The polymer composition of claim 1, wherein the composition further comprises at least one synthetic polymer.

18. The polymer composition of claim 17, wherein the synthetic polymer is a polythene, polystyrene, polyacrylate, polyamide, polyester, polyurethane, polysulfide, or polycarbonate.

19. The polymer composition of claim 17, wherein the synthetic polymer is polyethylene glycol.

20. The polymer composition of claim 1, wherein the C1 to C4 hydrocarbon groups are present at 30 mol % to 40 mol % with respect to amine groups of chitosan.

* * * * *